(12) United States Patent
Fertner et al.

(10) Patent No.: US 9,220,564 B2
(45) Date of Patent: Dec. 29, 2015

(54) ELECTROMAGNETIC RADIATION DELIVERY APPARATUS

(75) Inventors: Rembert Fertner, Klagenfurt (AT); Harald Robert, Klagenfurt (AT)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1715 days.

(21) Appl. No.: 11/917,470

(22) PCT Filed: Nov. 15, 2005

(86) PCT No.: PCT/IB2005/053757
§ 371 (c)(1),
(2), (4) Date: Jul. 16, 2010

(87) PCT Pub. No.: WO2006/134426
PCT Pub. Date: Dec. 21, 2006

(65) Prior Publication Data
US 2010/0276609 A1    Nov. 4, 2010

(30) Foreign Application Priority Data

Jun. 13, 2005   (EP) .................................... 05105141

(51) Int. Cl.
| | |
|---|---|
| A61B 18/18 | (2006.01) |
| A61B 18/20 | (2006.01) |
| A61B 18/00 | (2006.01) |
| A61B 19/00 | (2006.01) |
| A61N 5/06 | (2006.01) |

(52) U.S. Cl.
CPC ............. *A61B 18/203* (2013.01); *A61B 18/20* (2013.01); *A61B 2018/00452* (2013.01); *A61B 2018/00636* (2013.01); *A61B 2019/465* (2013.01); *A61N 2005/0644* (2013.01)

(58) Field of Classification Search
USPC ................. 606/9; 607/1, 2, 88, 94, 100, 101; 600/1; 250/491.1, 492.1, 493.1, 504 R
See application file for complete search history.

(56) References Cited

U.S. PATENT DOCUMENTS

| | | | | |
|---|---|---|---|---|
| 3,697,755 | A | * | 10/1972 | Boissevain et al. ........ 250/496.1 |
| 5,938,589 | A | * | 8/1999 | Wako et al. .................... 600/159 |
| 6,187,001 | B1 | | 2/2001 | Azar |
| 2002/0062142 | A1 | * | 5/2002 | Knowlton ............... A45D 44/22 607/99 |
| 2003/0065314 | A1 | | 4/2003 | Altshuler |
| 2004/0167499 | A1 | | 8/2004 | Grove |
| 2004/0176754 | A1 | | 9/2004 | Island |
| 2006/0241573 | A1 | * | 10/2006 | Roersma et al. ................... 606/9 |

FOREIGN PATENT DOCUMENTS

| | | | | |
|---|---|---|---|---|
| WO | 2005009266 | | 2/2005 | |
| WO | WO 2005/009266 | * | 2/2005 | ............. A61B 18/20 |
| WO | 2005093319 A1 | | 10/2005 | |

* cited by examiner

*Primary Examiner* — Nicole Ippolito

(57) ABSTRACT

An electromagnetic radiation delivery apparatus for tissue treatment, including a source of electromagnetic radiation, an emission window which is optically coupled to the source of electromagnetic radiation and is able to emit electromagnetic radiation, at least one recess provided in a skin contact area, and a pressure gauge for measuring a pressure inside the recess or a pressure correlated therewith. The electromagnetic radiation delivery apparatus for tissue treatment includes a pump for creating an overpressure inside the recess.

15 Claims, 8 Drawing Sheets

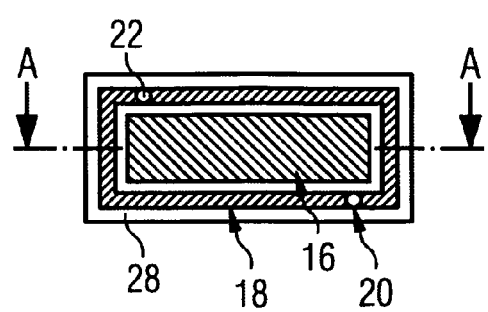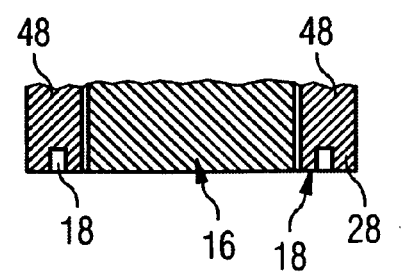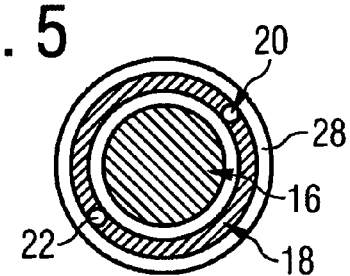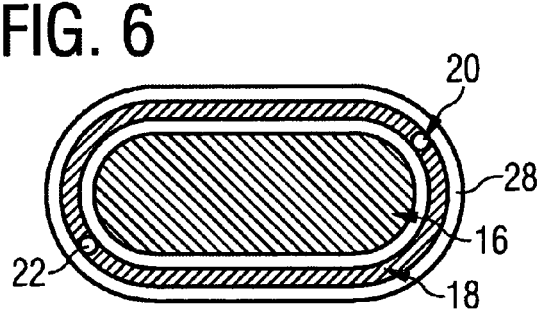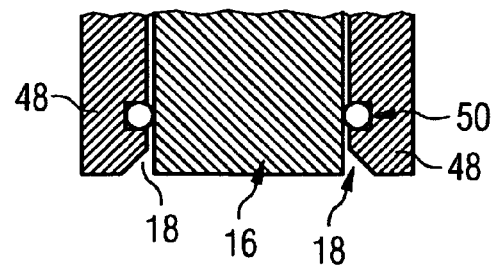

FIG. 14A
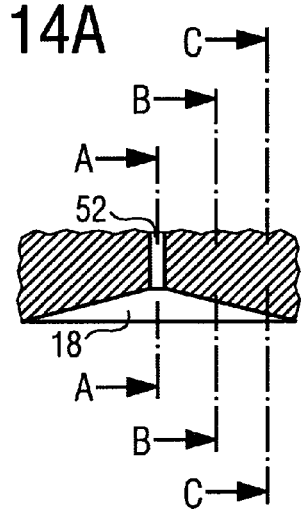
FIG. 14B A-A
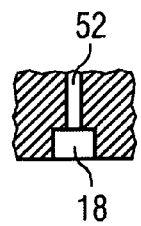
FIG. 14C B-B
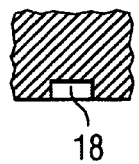
FIG. 14D C-C
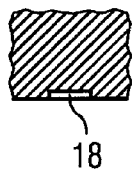
FIG. 15
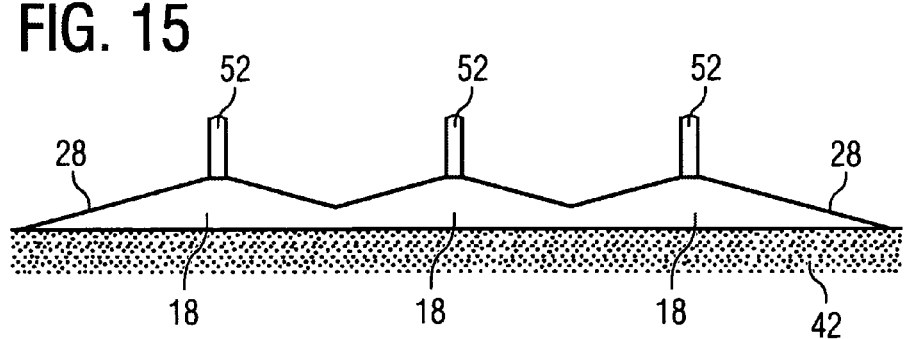

ELECTROMAGNETIC RADIATION DELIVERY APPARATUS

The present invention relates to an electromagnetic radiation delivery apparatus for tissue treatment, comprising a source of electromagnetic radiation, an emission window which is optically coupled to the source of electromagnetic radiation and is able to emit electromagnetic radiation, at least one recess provided in a skin contact area, and a pressure gauge for measuring a pressure inside the recess or a pressure correlated therewith.

An apparatus of the type mentioned above is known from WO 2005/009266 A1. The device disclosed in this document comprises vacuum means for creating an underpressure in the recess. The underpressure can only be built up or maintained, if the radiation delivery head of the apparatus is in proper contact with the skin to be treated. If the radiation delivery head is not in proper contact with the skin to be treated, the underpressure in the recess can not be built up or it collapses. This is detected via the pressure gauge to make sure that no electromagnetic radiation is emitted that could, due to the improper contact of the radiation delivery head and the skin to be treated, reach body parts not to be treated, such as eyes or skin parts of humans or animals nearby or even other objects susceptible to being damaged by the electromagnetic radiation.

A disadvantage of the apparatus known from WO 2005/009266 A1 is that movement of the apparatus over the skin may be hampered due to the underpressure leading to skin being sucked into the recess.

It is the object of the present invention to further develop the apparatuses of the kind mentioned at the beginning such that movement of the apparatus over the skin is facilitated.

This object is solved by the features of the independent claims. Further developments and preferred embodiments of the invention are outlined in the dependent claims.

In accordance with the present invention there is provided an electromagnetic radiation delivery apparatus for skin treatment of the type mentioned at the beginning which comprises means for creating an overpressure inside the recess. Preferably, the means for creating the overpressure are formed by an electric air pump which feeds compressed air into the recess. However, other gases than air may be also used, if this is regarded as advantageous for certain kinds of skin treatments. The overpressure in the recess leads to a little leakage, i.e. a part of the compressed air is pressed out of the recess. Therefore, a cushion of air (or of another gas) is created on which the skin contact area is placed. This ensures that the apparatus may be easily moved over the skin to be treated. The pressure gauge may be a pressure meter combined with a display, a switch or other control means.

A preferred embodiment of the apparatus according to the invention is further characterized by control means connected to the pressure gauge and to the source of electromagnetic radiation, wherein the control means are able to prevent the electromagnetic radiation source and/or the emission window from emitting electromagnetic radiation when the pressure measured by the pressure gauge is lower than a predetermined threshold value. Thereby, the risk of incorrect use is lowered even further. The control means may be provided as for instance an electronic switch or shutter. If an appropriate threshold value is set, it is not possible to operate the apparatus when the pressure is below that predetermined value because there is no proper contact between the skin contact area and the skin to be treated. Consequently, even in the case of operation by unfit people, e.g. small children, the risk of causing harm or danger is reduced. It is to be noted that in the context of the present application, "measuring" a pressure means either determining an absolute value, or determining a relative value, e.g. with respect to the predetermined threshold value. In that case it is not necessary to determine the true pressure value, but only whether the pressure is above or below the threshold value. The threshold value, i.e. the pressure value below which the apparatus should be turned off or is automatically turned off by the control means may be appropriately selected in accordance with the properties of the body part or surface to be treated.

Advantageously, the threshold value is from 1 to 500 mbar above ambient pressure. If the body part or surface to be treated is smooth, flexible and compressible, a low pressure difference may be selected, e.g. 10 or 20 mbar above ambient pressure. If the surface to be treated is rough and incompressible, the threshold value should be much higher than ambient pressure, e.g. 200 mbar, in order to ensure a correct check of the position of the skin contact area. As mentioned above, it is advantageous that part of the compressed air leaks out of the recess even when the delivery head is in the correct position. The power of the overpressure means should therefore be high enough for a sufficient pressure difference to be maintained in spite of the leaking of air. Of course the threshold value can depend on the ambient pressure, which means that e.g. in an area of low pressure or at a high altitude; the threshold value is correspondingly lower than the threshold value in an area of high pressure or at sea level. Preferably, the threshold value depends on the ambient pressure and it may be expressed as a pressure difference with ambient pressure. In the presently preferred embodiment it is possible to define the threshold value as a pressure difference with ambient pressure of between 1 and 500 mbar.

Preferably, during a period of time in which the measured pressure inside the recess is below the threshold value, the control means are able to prevent the electromagnetic radiation source from emitting electromagnetic radiation above a predetermined maximum amount of energy. By allowing only a certain maximum amount of energy to be emitted during a session, overexposure of the skin, with possible (increased) discomfort or injury may be avoided. Moreover, there will be no more uncertainty whether or not a certain part of the skin received radiation. Since the electromagnetic radiation which is delivered to the body part or surface to be treated affects said body part or surface, it may be important to limit the total amount of supplied radiation. In a preferred embodiment, the control means are able to prevent re-operation of the apparatus, thereby ensuring that it is not possible to supply more radiation energy than the predetermined maximum amount of energy without lifting the delivery head and hence breaking the overpressure.

At least for some application areas it is advantageous that the control means control a shutter that is able to prevent emission of the electromagnetic radiation. Such a shutter may take any desired form, e.g. an electro-optical shutter, a mechanical shutter, a switchable mirror etc. An advantage of the presence of such a shutter is that the electromagnetic radiation source need not be switched off when the apparatus is not to emit radiation. For many sources of electromagnetic radiation this is beneficial to the lifetime of the source. However, if frequent switching on and off of the electromagnetic radiation source does not substantially shorten the lifetime of the source, it is also possible for the control means to simply switch the power source of the electromagnetic radiation source on and off, for example in the case of LEDs and lasers.

In one embodiment, an emission window is present in the recess. The term "emission window" relates to an area, for example of a radiation delivery head, through which electromagnetic radiation is emitted. It may come in the form of e.g. a piece of material that is transparent to the electromagnetic radiation to be emitted, e.g. glass in the case of optical light. However, it may also mean an open side of a cavity which is not covered by any material, e.g. an exit end of a tube. An advantage of an emission window being present in the recess is that when the recess is deemed to be positioned correctly, the emission window is automatically positioned correctly as well. In most cases, one emission window is present. However, it is to be noted that it is also possible for a plurality of emission windows to be present.

With another embodiment the recess surrounds the emission window. This is a slightly more general instance of the case in which the emission window is present in the recess. If the recess surrounds the emission window, then an appropriate overpressure in the recess guarantees a correct positioning of the emission window. In this case the recess may come in the form of a groove around the emission window. In this way it is possible to have different shapes for the recess and the emission window. This offers advantages if the radiation is preferably supplied in a circular pattern, e.g. for homogeneity reasons, whereas a different part of the surface surrounding the part which is treated should not receive radiation. This part may of course have a different shape. Furthermore, it is also possible that a plurality of recesses is provided. It may be contemplated that a number of small recesses is present in the form of a number of holes around the emission window. If all holes are positioned correctly, this too is a safe indication that the delivery apparatus is positioned correctly.

For all embodiments it may be advantageous that the recess comprises a circumferential edge. In this way it is relatively simple to visually check the correct positioning by inspecting the circumferential edge.

Advantageously, the circumferential edge is flexibly deformable. This embodiment allows adaptation to a body part or surface not exactly matching the plane of the emission window or recess. Although it is possible to use a non-deformable skin contact area and delivery head, respectively, and to make use of the deformability of the body part or a surface to be treated, a flexibly deformable circumferential edge offers the advantage that the pressure exerted on the body part or surface differs less. If the emission window is in the form of a transparent piece of material, this piece of material may be used to exert pressure on the body part or surface to be treated. In this case, in particular in the case of skin, the bloodstream through said body part may be affected. For instance in the case of photo hair removal, it is advantageous if the blood circulation is reduced in the tissue being treated, because then there will be less absorption of radiation by tissue parts other than the intended parts (chromophores, hair follicles). Besides, risks of possible side-effects of the treatment are reduced. The flexibly deformable circumferential edge may be designed as a rim of resilient material such as rubber. Any other flexibly deformable material or construction is also possible.

In an advantageous embodiment, the circumferential edge lies on a plane surface, on a concave surface or on a convex surface. With these simple geometries, most body parts or other surfaces to be treated can be treated efficiently. Plane surfaces may be used for treating e.g. artificial objects or small areas of large and hence relatively flat body parts such as legs. A concave surface for the circumferential edge may be useful when treating a convex body part, e.g. a relatively small body part such as a finger or other, strongly curved body parts such as a nose. A convex surface for the circumferential edge is advantageous for the treatment of more or less concave surfaces, such as for the depilation of arm pits. In specific cases other surfaces for the circumferential edge may be even more advantageous.

In a preferred embodiment of the apparatus according to the invention, the electromagnetic radiation comprises infrared radiation, visible optical radiation or ultraviolet radiation. For the purpose of the present application, infrared radiation, visible optical radiation and ultraviolet radiation will be referred to as "optical radiation". Optical radiation is a part of the electromagnetic spectrum which is most often used for the treatment of body parts, especially by non-skilled or other private persons. In principle, however, it would be possible to use other types of electromagnetic radiation, e.g. microwave radiation or x-rays. The preferred electromagnetic radiation according to the invention (optical radiation) covers treatments by means of heat (infrared radiation) for treatment of muscle pain, depilation, treatment of hyperbilirubinaemia, etc. by means of visible optical radiation, and artificial tanning and treatment of various skin disorders, such as vitiligo and psoriasis. Although some treatments may be performed by non-skilled or non-professional personnel, such as tanning and depilation, in many cases it may be preferable to have professional skilled personnel perform the treatment. Nevertheless, also in the case of professional personnel, the improved safety and other advantageous features of the apparatus according to the invention are valid. Throughout the application the words "body part" and "surface to be treated" relate to any human tissue susceptible to a treatment by means of electromagnetic radiation. In particular this relates to skin (human skin). In general, however, any other treatable surface may be contemplated, e.g. in the field of materials research, curing of material. However, the invention has special advantages when used in relation to treatment of humans or animals, since the risks of inadvertent injury through accidents etc. are much reduced.

In the apparatus according to the present invention, the source of electromagnetic radiation may be arranged in a radiation delivery head. This means that e.g. a light source such as a LED or a high-pressure gas discharge lamp is built into the radiation delivery head. However, in an advantageous embodiment, the source of electromagnetic radiation comprises electromagnetic radiation generating means and electromagnetic radiation guiding means optically connected thereto. The presence of an electromagnetic radiation generating means and electromagnetic radiation guiding means offers the possibility of separation of these two functions. This means that a complex, large and heavy electromagnetic radiation generating means, such as a high power laser, may be present at a certain distance from the delivery head. The delivery head, which eventually emits the radiation generated by the electromagnetic radiation generating means is optically connected to the electromagnetic radiation guiding means so that the latter can guide the electromagnetic radiation to the radiation delivery head, and eventually to the emission window. This allows a relatively small and lightweight delivery head, which greatly improves the ease of use of the apparatus.

In an advantageous embodiment, the electromagnetic radiation guiding means comprise a mirror, a hollow electromagnetic radiation guide or an optical fiber. The person skilled in the art will know how to select the appropriate guiding means. E.g. in the case of a laser, an optical fiber may be the guiding means of choice. A mirror may be used in the case where a laser is the electromagnetic radiation generating means and the laser beam is used to scan a certain area to be treated. This allows said area to be illuminated homogeneously by the laser beam without the operator having to move the radiation delivery head. This greatly improves the efficacy and homogeneity of the treatment.

Advantageously, the source of electromagnetic radiation comprises a laser, a flash lamp, a LED, a gas discharge lamp or an incandescent lamp. These electromagnetic radiation sources have proved to be efficient and useful in a wide variety of possible uses of the apparatus according to the invention. They come in a large variety of wavelengths, powers etc. Nevertheless, in particular cases, other sources may be used also, such as x-ray sources.

Advantageously, the at least one recess is formed by a groove having a depth which is greater than the width of the groove. The cross section of the groove, i.e. the relation between width and depth, is very important. If the width of the groove is, for example, not larger than 3 mm, the skin cannot touch the inner side of the groove even if it is pressed very strong against the device and vice versa. Skin doming can not close the overpressure air supply of the groove. In general, different cross sections of the groove are possible, for example rectangular, squared, half-rounded, triangular, or rounded triangular.

Additionally or alternatively it is possible that the recess is at least partly formed in the emission window, particularly in the surface of the emission window which is intended to contact the skin. There may, for example, be provided grooves that are placed (also) on or in the exit window surface in such a way, that the overpressure air flows over the surface in order to cool the skin. The shape of the groove on the surface is, for example, meander-like arranged, or the air flows from one to the other side in parallel groves. If there is a recessed window, the air, for example, flows also from one corner of the arrangement to the other one.

In accordance with a further development of the present invention, the recess is formed in a treatment head of the apparatus, wherein at least a part of the recess is arranged pivotable with respect to other components of the treatment head. For example, the overpressure groove-system can be mounted pivotable around the emission window which may be, for example, an astigmatic/cylindrical lens or a convex lens. If the hand piece of the treatment head, where the optical- and overpressure-system can be integrated, is pivoted on the skin, the overpressure system and the lens is always in contact with the skin. They are laying in a plane surface. At least in some cases it may be advantageous, if the pivotable overpressure system is spring loaded with respect to the hand piece.

For the apparatus according to the invention it is preferred that there are provided at least two overpressure ducts for creating the overpressure in the at least one recess. In general providing at least two overpressure ducts for each recess minimizes the risk that the overpressure can not be build up due to a clogged duct.

The above and further aspects and advantages of the invention will be apparent from and elucidated with reference to the embodiments described hereinafter and shown in the drawings, wherein:

FIG. 4A shows a bottom view of a treatment head of a fourth embodiment of the apparatus in accordance with the present invention;

FIG. 4B shows a sectional view of a part of the treatment head of FIG. 4A;

FIG. 5 shows a bottom view of a treatment head of a fifth embodiment of the apparatus in accordance with the present invention;

FIG. 6 shows a bottom view of a treatment head of a sixth embodiment of the apparatus in accordance with the present invention;

FIG. 7 shows a sectional view of a treatment head of a seventh embodiment of the apparatus in accordance with the present invention;

Figure 9:
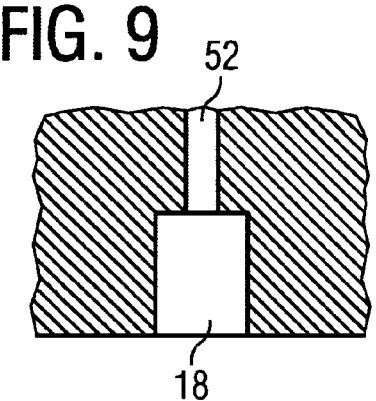
Figure 10:
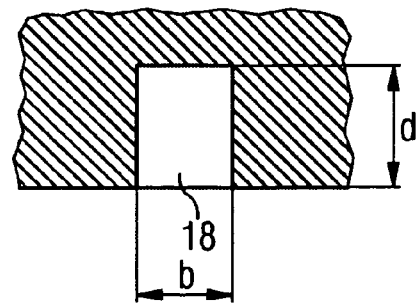
Figure 11:
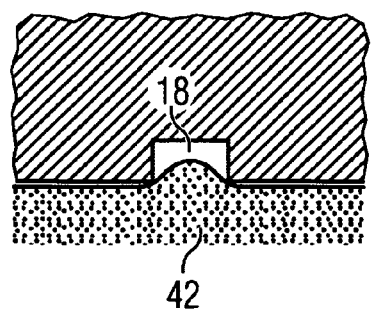
Figure 12:
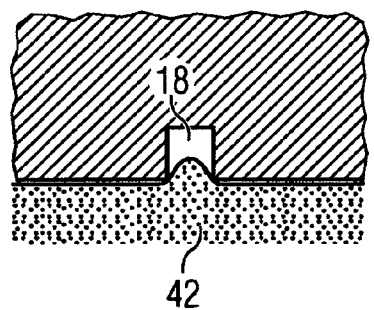
Figure 13:
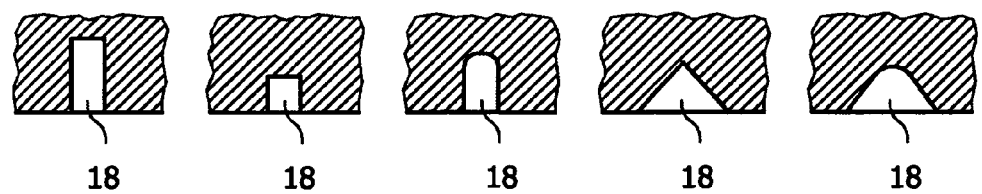
Figure 16:
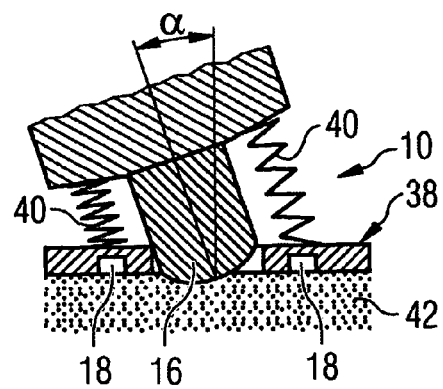
Figure 17A:
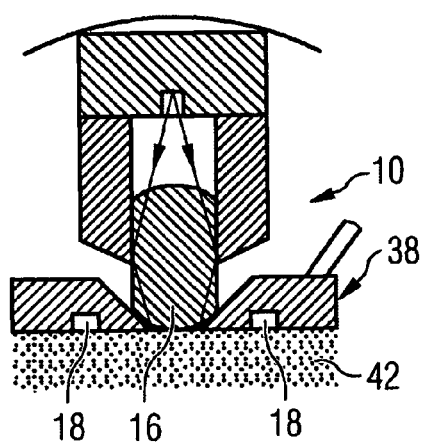
Figure 17B:
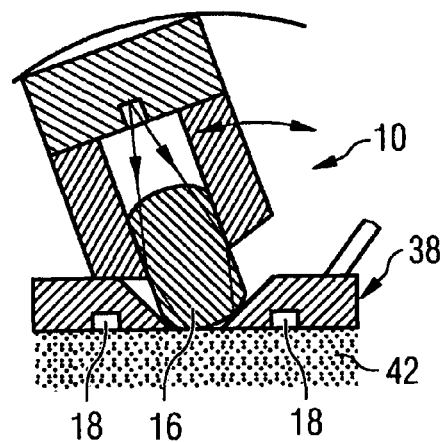
Figure 18A:
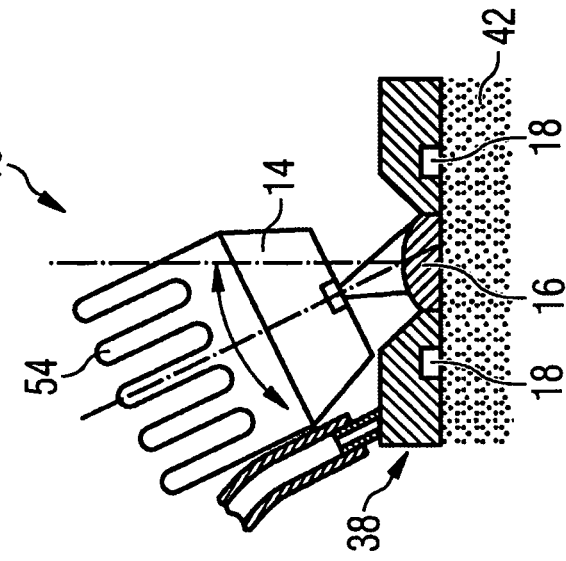
Figure 18B:
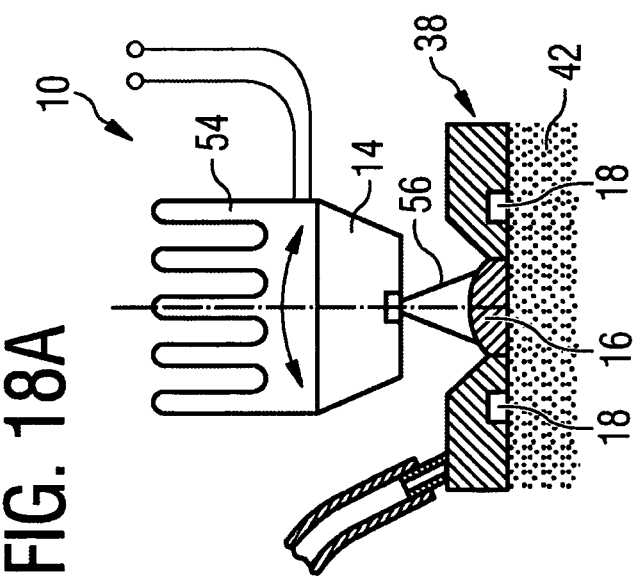

FIG. 9 schematically illustrates a possibility for feeding air into a recess;

FIG. 10 schematically illustrates a preferred geometry of a groove forming the recess or being part thereof;

FIG. 11 shows an undesired skin doming effect resulting from a disadvantageous geometry of a groove;

FIG. 12 shows a reduces skin doming effect resulting from a advantageous geometry of a groove;

FIG. 13 illustrates examples for possible cross sections of a groove forming the recess or being part thereof;

FIG. 14A shows a groove having a triangular cross section together with an overpressure feeding duct associated to the groove;

FIGS. 14B, 14C, and 14D are cross sectional views corresponding to the section lines A-A, B-B, and C-C of FIG. 14A;

FIG. 15 schematically illustrates a possible arrangement of adjacent grooves;

FIG. 16 shows an emission window in the form of a convex lens, wherein an overpressure system is arranged pivotable with respect to the emission window and the further components of a treatment head;

FIG. 17A shows an emission window in the form of an astigmatic/cylindrical lens, wherein an overpressure system is arranged pivotable with respect to the emission window and the further components of a treatment head;

FIG. 17B shows the arrangement of FIG. 17A in a tilted position;

FIG. 18A shows an example for a recessed, concave or convex emission window which is surrounded by an overpressure ring system, wherein the overpressure ring system is pivotable with respect to the emission window and the further components of a treatment head; and FIG. 18B shows the arrangement of FIG. 18A in a tilted position;

Throughout the drawings equal or similar reference numerals are used to denote equal or similar components, and at least some of these components are explained only once to avoid repetitions.

Figure 1:
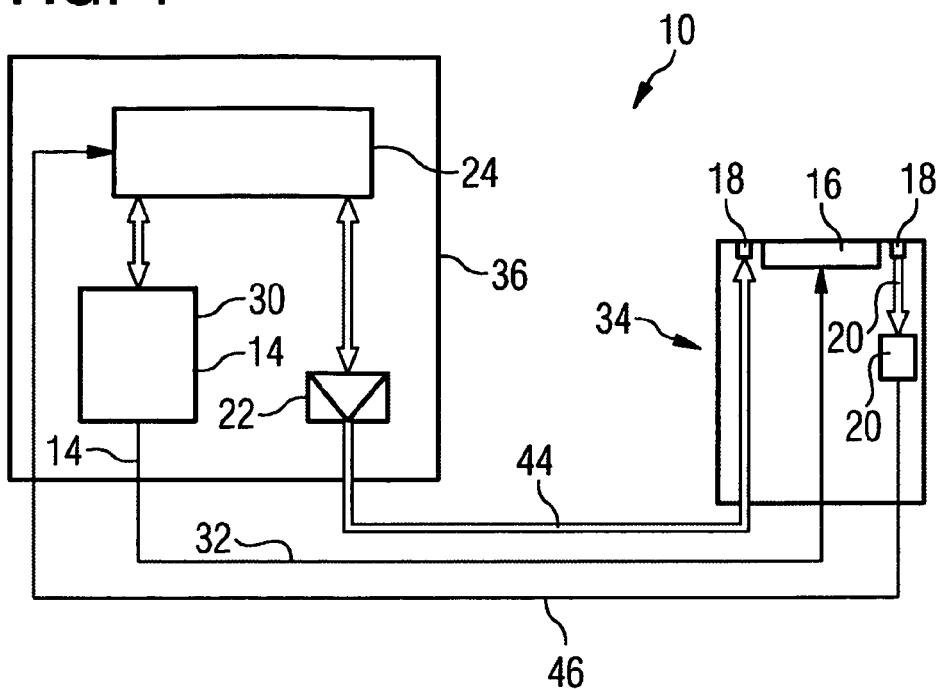
FIG. 1 shows a schematic block diagram of a first embodiment of the apparatus in accordance with the present invention, wherein the apparatus comprises a main device and a treatment head connected thereto.

FIG. 1 shows a schematic block diagram of a first embodiment of the apparatus 10 in accordance with the present invention, wherein the apparatus comprises a main device 36 and a treatment head 34 connected thereto. The main device 36 comprises a source of electromagnetic radiation 14 consisting of an electromagnetic radiation generation means 30 and electromagnetic radiation guiding means 32. The electromagnetic radiation generating means 30 may comprise a laser, a flash lamp, a LED, a gas discharge lamp or an incandescent lamp. However, if the electromagnetic radiation generating means 30 are located in the main device 36, it is preferred that a laser generates the radiation. The source of electromagnetic radiation 14 furthermore comprises radiation guiding means 32, which are shown as an optical fiber in FIG. 1 but can also comprise a mirror or a hollow electromagnetic radiation guide and/or a radiation guiding crystal, particularly a crystal comprising a total internal reflection. The optical fiber 32 guides the electromagnetic radiation to an emission window 16 which is located in the treatment head 34. The main device 36 furthermore comprises means 22 for creating an overpressure, wherein the means 22 can be formed for example by a suitable pump, as illustrated. By a pressure line 44 the pump 22 is connected to a recess 18 provided in the skin contact area of the treatment head 34. In the treatment head 34 there is further provided a pressure gauge 20 for detecting the pressure inside the recess 18. The source of electromagnetic radiation 14 as well as the pump 22 are controlled by control means 24 which receive the output signal of the pressure gauge 20 via a wire 46. As may be seen, the control means 24 are located within the main device 36, and the control means 24 can, for example, comprise a microprocessor, memory means and further circuitry well known to the person skilled in the art.

The apparatus 10 can, for example, be a depilation apparatus. To prevent that electromagnetic radiation generated by the source of electromagnetic radiation 14 and emitted by the emission window 16 reaches regions, for example, an eye of the user, the apparatus 10 works as follows. If the treatment head 34 is in a proper contact with the skin to be treated, an overpressure is built up in the recess 18 which is formed by a groove which completely surrounds the emission window 16. This overpressure is detected by the pressure gauge 20 which feeds his output signal to the control means 24. If the control means 24 detect that the overpressure is sufficiently high, it is assumed that the treatment head 34 is in proper contact with the skin to be treated and the control means 24 instruct the electromagnetic radiation generation means 30 to generate radiation which is fed to the skin to be treated via the optical fiber 32 and the emission window 16. If the overpressure in the recess 18 decrease due to an improper contact of the treatment head 34 and the skin to be treated, the control means 24 detect the drop in pressure via the output signal of the pressure gauge 20. To avoid that the user (or any other person) is hurt by radiation, the control means 24 immediately instructs electromagnetic radiation generating means 30 to stop generating radiation. In case of a proper contact between the treatment head 34 and the skin to be treated, a cushion of air is created on which the skin contact area of the treatment head 34 can glide during operation. Furthermore, an overpressure has the advantage that clogging of the opening or openings will be hampered. As soon as there is dirt or any kind of impurity, the little air flow out of the openings help to blow away these impurities, like skin flakes from tissue (epidermis), dust or something like this.

Figure 2:
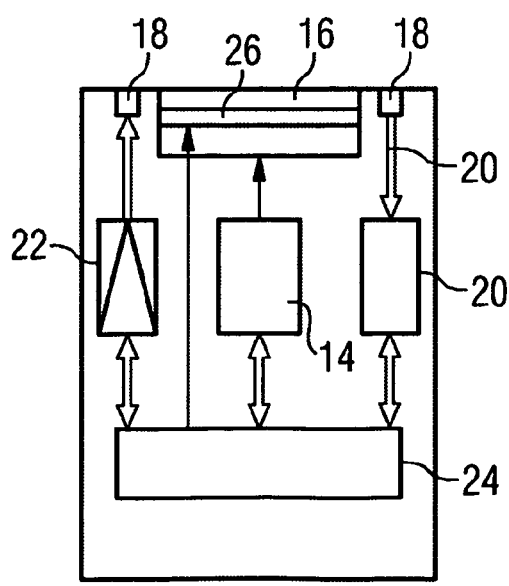
FIG. 2 shows a schematic block diagram of a second embodiment of the apparatus in accordance with the present invention, wherein the apparatus is completely formed by a hand piece.

FIG. 2 shows a schematic block diagram of a second embodiment of the apparatus 10 in accordance with the present invention. The components shown FIG. 2 essentially correspond to the components discussed with reference to FIG. 1, and, to avoid repetitions, reference is made to the corresponding description. However, with the embodiment shown in FIG. 2, the apparatus 10 is completely formed by a hand piece, and therefore, all components are arranged within the hand piece. In addition to the components discussed with reference to FIG. 1, the embodiment of FIG. 2 further comprises a shutter 26 which is suitable to cover the emission window 16 such that no radiation is emitted, even if radiation is generated by the source of electromagnetic radiation 14. The shutter 26 is activated by the control means 24, if an insufficient overpressure in the recess 18 surrounding the emission window 16 is detected due to an improper contact of the skin contact area and the skin to be treated.

Figure 3A:
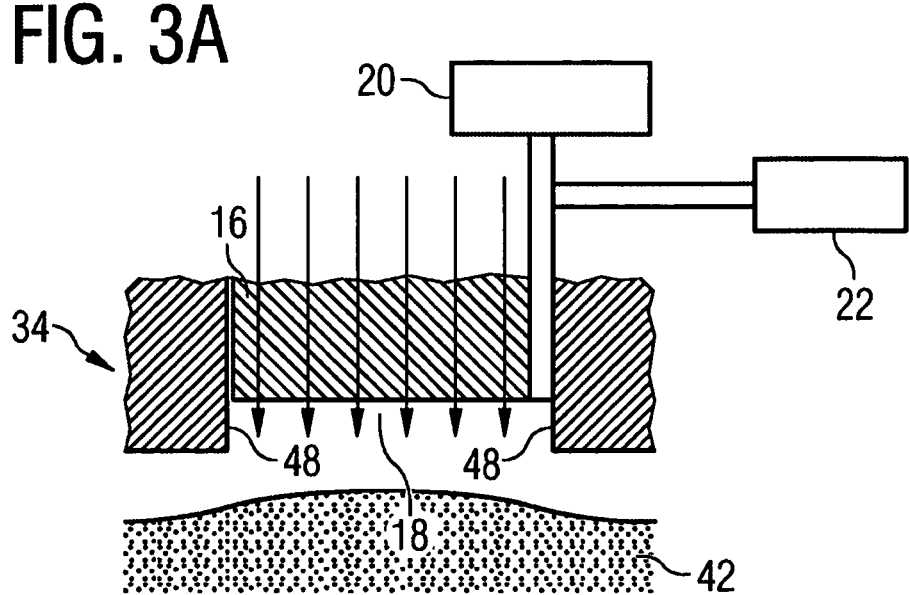
FIG. 3A shows a schematic block diagram of a part of a treatment head of a third embodiment of the apparatus in accordance with the present invention, wherein emission window is recessed with respect to the surrounding material.
Figure 3B:
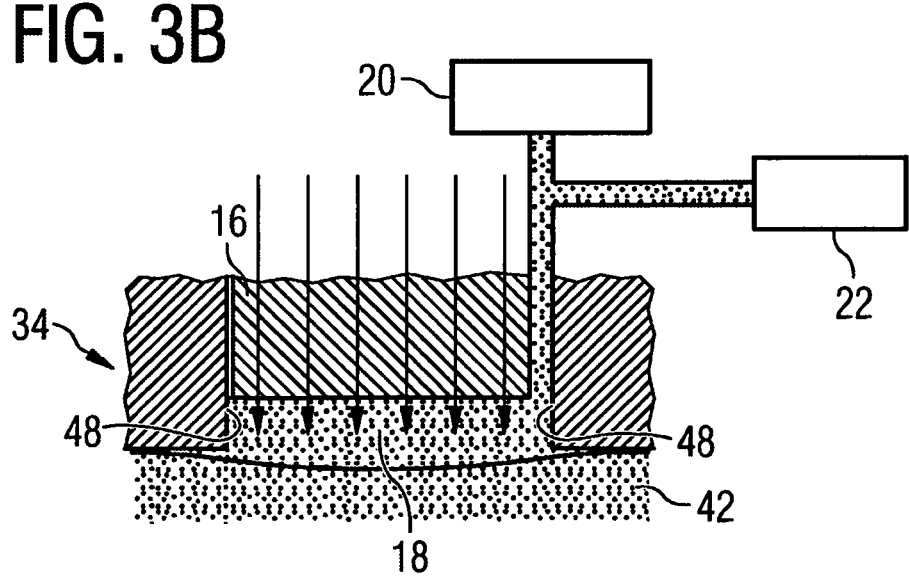
FIG. 3B shows the part of the treatment head of FIG. 3A during treatment of skin.

FIG. 3A shows a schematic block diagram of a part of a treatment head 34 of a third embodiment of the apparatus 10 in accordance with the present invention, wherein emission window 16 is recessed with respect to the surrounding material 48, and FIG. 3B shows the part of the treatment head 34 of FIG. 3A during treatment of skin 42. Between the transparent emission window 16, where the radiation is coming out, and the skin 42 to be treated, there is a certain distance of a couple of millimeters forming a recess 18. The surrounding material 48 is reflective or at least not transparent, or it consists of a material that scatters the light like skin. Aim is not to lose radiation that is scattered back from the skin to the surrounding material 48. As may be seen in FIG. 3B, this arrangement is pressed onto the skin 42 during treatment. Between the emission window 16 and the skin 42 a cavity of recess 18 is formed. A pump 22 produces an overpressure in the recess 18, similar as described above for the recess 18 in form of a groove. If the edges of the surrounding material 48 around the emission window 16 are pressed quite well to the skin 42, the pressure in the recess 18 can increase to a defined level which has to be higher than the air pressure that is available around the device, as discussed above. As regards the safety function of this arrangement, reference is made to the corresponding description in connection with FIG. 1.

FIG. 4A shows a bottom view of a treatment head of a fourth embodiment of the apparatus in accordance with the present invention, and FIG. 4B shows a sectional view of a part of the treatment head of FIG. 4A. As may be seen, with this embodiment the skin contact area comprises a rectangular geometry. The emission window 16 is surrounded by a recess 18 in form of a groove. The groove 18 is connected to a pressure gauge 20 and a pump 22, as discussed with reference to FIG. 1. As may be best seen in FIG. 4B, the emission window and the surrounding material 48 form a common skin contact plane. The surrounding material 48 forms a circumferential edge 28 which may be flexibly be formable to enhance the ceiling function.

FIG. 5 shows a bottom view of a treatment head of a fifth embodiment of the apparatus in accordance with the present invention. With this embodiment the skin contact area comprises a circular geometry. Except that, the configuration corresponds to the embodiment of FIG. 4A and FIG. 4B.

FIG. 6 shows a bottom view of a treatment head of a sixth embodiment of the apparatus in accordance with the present invention. With this embodiment, the skin contact area comprises a substantially rectangular geometry; however, the corners and the groove are rounded. Except that, the configuration corresponds to the embodiment of FIGS. 4A and 4B.

FIG. 7 shows a sectional view of a treatment head of a seventh embodiment of the apparatus in accordance with the present invention. With this embodiment the recess or groove 18 is not separately formed but is formed partly by the emission window 16 and the slanted edge of the surrounding material 48. With such an arrangement it is advantageous to provide a suitable sealing 50 between the emission window 16 and the surrounding material 48.

Figure 8A:
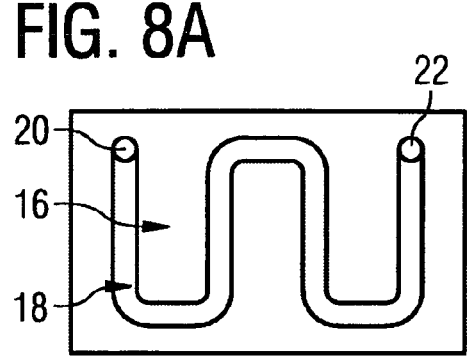
FIG. 8A shows a bottom view of a treatment head of an eighth embodiment of the apparatus in accordance with the present invention.
Figure 8B:
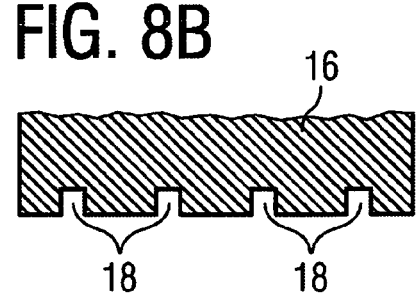
FIG. 8B shows a sectional view of a part of the treatment head of FIG. 8A.

FIG. 8A shows a bottom view of a treatment head of an eight embodiment of the apparatus in accordance with the present invention, and FIG. 8B shows a sectional view of a part of the treatment head of FIG. 8A. With this embodiment the recess 18 is at least partly formed in the skin contact area of the emission window 16. As may be seen a meander-like groove 18 is provided, which is connected to the pressure gauge 20 and the pump 22. Thereby, the overpressure air is flowing on the surface and cools the skin which is treated.

FIG. 9 schematically illustrates a possibility for feeding air into a recess 18. As may be seen, the recess 18 is provided in form of a groove having a rectangular cross section. A duct 52, which may be regarded as a part of the overpressure generating means 22, is provided to feed air into the recess 18. A similar duct may be provided on the other end of the groove to connect the recess 18 with the pressure gauge.

FIG. 10 schematically illustrates a preferred geometry of a groove forming the recess or being part thereof. The cross section, i.e. the relation between width and depth of the groove, is very important. Best results may be obtained, if the width at the skin contact area is smaller than the depth of the groove. If the width of the groove 18 is, for example, not more than 3 mm, the skin can not touch the inner side of the groove 18, even if it is pressed very strong to the device and vice versa.

FIG. 11 shows an undesired skin doming effect resulting from a disadvantageous geometry of a groove. As may be seen, if the groove 18 is not deep enough, it is possible that skin touches the inner side of the groove, and in the worst case seals the duct leading to the pressure gauge, whereby the safety function could be disabled.

FIG. 12 shows a reduced skin doming effect resulting from an advantageous geometry of a groove. As may be seen, skin doming still occurs, but the skin can not touch the inner side of the groove since the depth of the groove is greater than the width thereof.

FIG. 13 illustrates examples for possible cross sections of a groove forming the recess or being part thereof. From the left to the right the following cross sections of a groove 18 are shown: rectangular, squared, half-rounded, triangular, and rounded-triangular. All these geometries may be used, while it is still preferred that the width of the groove 18 is smaller than the depth thereof.

FIG. 14A shows a groove having a triangular cross section together with an overpressure feeding duct 52 associated to the groove 18 and FIGS. 14B to 14D are cross sectional views corresponding to the section lines A-A, B-B, and C-C of FIG. 11A. As may be seen from FIGS. 14A and 14B it is preferred that the duct 52 for feeding the pressurized air is located in the centre. This is preferred to avoid that the duct 52 is clogged by the skin doming.

FIG. 15 schematically illustrates a possible arrangement of adjacent grooves 18. There are shown three adjacent grooves 18, each having a triangular cross section and a central duct 52 for feeding pressurized air. The grooves 18 overlap and the sealing function with reference to the skin 42 is provided by the circumferential edges 28.

FIG. 16 shows an emission window 16 in the form of a convex lens, wherein an overpressure system 38 is arranged pivotable with respect to the emission window 16 and the further components of a treatment head 34. If the hand piece or treatment head 34, in which the optical system and/or the overpressure pump may be integrated, is pivoted or treated with respect to the skin 42, the overpressure system 38 comprising the groove 18 and the convex lens is always in contact with the skin 42. It may be advantageous, if the overpressure system 38 is spring loaded by springs 40 to achieve an optimal contact between the overpressure system 38 and the skin 42.

FIG. 17A shows an emission window 16 in the form of an astigmatic/cylindrical lens, wherein an overpressure system 38 is arranged pivotable with respect to the emission window 16 and the further components of a treatment head, and FIG. 17B shows the arrangement of FIG. 17A in a tilted position. Except the lens configuration and the missing springs, the embodiment of FIGS. 17A and 17B is similar to the embodiment of FIG. 16.

FIG. 18A shows an example for a recessed, concave or convex emission window 16 which is surrounded by an overpressure ring system 38, wherein the overpressure ring system 38 is pivotable with respect to the emission window 16 and the further components of a treatment head 34, and FIG. 18B shows the arrangement of FIG. 18A in a tilted position. The configuration of the embodiment shown in FIGS. 18A and 18B is very similar to the configuration shown in FIG. 16. However, in accordance with the embodiment of FIGS. 18A and 18B the hand piece comprises a heat sink 54 to dissipate heat generated by the source of electromagnetic radiation 14. Furthermore, with the illustrated embodiment, it is preferred that there is provided an AR-coating on parts of the emission window 16. With such an arrangement radiation passes the emission window 16 without losses, independent of the angle between the overpressure system 38 and the emission window 16. The light-unit is mounted pivotable around the central axis of the emission window 16. Although not shown, the overpressure system may be spring loaded, as discussed in connection with FIG. 16.

Equivalents and modifications not described above may also be employed without departing from the scope of the invention, which is defined in the accompanying claims.

The invention claimed is:

1. An electromagnetic radiation delivery apparatus having a source of electromagnetic radiation for tissue treatment, the apparatus comprising:
   a skin contact area including
      an emission window optically coupled to the source of electromagnetic radiation for emitting electromagnetic radiation, and
      at least one recess provided in the skin contact area;
   a pressure gauge for measuring a pressure inside the at least one recess or a pressure correlated therewith;
   a pump configured to create an overpressure inside the at least one recess; and
   a controller coupled to the pressure gage and the source of electromagnetic radiation and configured to detect the overpressure to determine skin contact and to control the electromagnetic radiation to be emitted when overpressure is detected and to stop emission of the electromagnetic radiation when the overpressure is below a predetermined threshold value.

2. The apparatus according to claim 1, wherein the controller is coupled to the pump to control the pump.

3. The apparatus according to claim 2, wherein the threshold value is above ambient pressure.

4. The apparatus according to claim 1, comprising a shutter, wherein the controller controls the shutter to prevent emission of the electromagnetic radiation.

5. The apparatus according to claim 1, further comprising a treatment head including the emission window.

6. The apparatus according to claim 1, wherein the at least one recess is a plurality of recesses smaller than the emission window.

7. The apparatus according to claim 6, wherein the at least one recess comprises a circumferential edge.

8. The apparatus according to claim 7, wherein the circumferential edge is flexibly deformable.

9. The apparatus according to claim 7, wherein the circumferential edge lies on a plane surface, on a concave surface or on a convex surface.

10. The apparatus according to claim 1, wherein the at least one recess is formed by a groove having a depth which is greater than the width of the groove.

11. The apparatus according to claim 1, wherein the at least one recess is at least partly formed in the emission window.

12. The apparatus according to claim 1, wherein the emission window is pivotably arranged.

13. The apparatus according to claim 1, further comprising at least two overpressure ducts connected to a top of each at least one recess for creating the overpressure in the at least one recess.

14. The apparatus according to claim 1, further comprising a handpiece wherein the source of electromagnetic radiation, the emission window, the pressure gage and the pump are configured as a portion of the handpiece.

15. The apparatus according to claim 1, wherein the at least one recess comprises a groove that meanders through the skin contact area.

* * * * *